United States Patent [19]
Becht et al.

[11] 4,261,244
[45] Apr. 14, 1981

[54] SURGICAL STAPLE

[75] Inventors: Carl T. Becht, Cincinnati, Ohio; Robert G. Rothfuss, Bellevue, Ky.

[73] Assignee: Senco Products, Inc., Cincinnati, Ohio

[21] Appl. No.: 38,579

[22] Filed: May 14, 1979

[51] Int. Cl.³ .................... A61B 17/04; A61B 17/08; F16B 15/00
[52] U.S. Cl. .................... 411/472; 128/337; 128/334 R; 227/DIG. 1
[58] Field of Search ............... 128/337, 334, 335; 85/49; 227/DIG. 1, 120, 130

[56] References Cited
U.S. PATENT DOCUMENTS

| | | | |
|---|---|---|---|
| 2,128,443 | 8/1938 | Vogel | 85/49 |
| 3,273,562 | 9/1966 | Brown | 128/337 |
| 3,357,296 | 12/1967 | Lefever | 85/49 |
| 3,363,628 | 1/1968 | Wood | 128/337 |
| 3,908,884 | 9/1975 | Schrepferman | 227/120 |
| 3,969,975 | 7/1976 | Krol | 85/49 |

FOREIGN PATENT DOCUMENTS 931044  8/1955  Fed. Rep. of Germany .............. 85/49

*Primary Examiner*—Robert W. Michell
*Assistant Examiner*—C. W. Shedd
*Attorney, Agent, or Firm*—Frost & Jacobs

[57] ABSTRACT

A surgical staple for use in suturing the skin or fascia of a patient. The surgical staple has an elongated, substantially horizontal crown portion terminating in downwardly depending leg portions having points formed at their free ends. The staple, together with a plurality of identical surgical staples, is adapted to straddle and to be fed along a guide means of a surgical stapling instrument to the anvil thereof. The crown of the surgical staple is formed about the anvil by the surgical stapling instrument former which bends end portions of the surgical staple crown downwardly so that the staple leg portions are substantially coaxial with their points approaching each other. The surgical staple has a first pair of diametrically opposed flats extending respectively along the front and rear of the crown and leg portions. The surgical staple has a second pair of diametrically opposed flats, disposed at 90° to the first pair of flats. One flat of the second pair extends along the upper surface of the staple crown portion and the outsides of the staple leg portions and the other flat of the second pair extends along the underside of the crown portion and along the insides of the leg portions. The flats of the first pair, cooperating with similar flats on adjacent surgical staples, assure proper feeding of the surgical staple along the surgical instrument guide means. The flats of the second pair, cooperating with the surgical stapling instrument former and anvil, prevent undesirable rotation of the staple crown portion during forming and implanting of the surgical staple.

3 Claims, 17 Drawing Figures

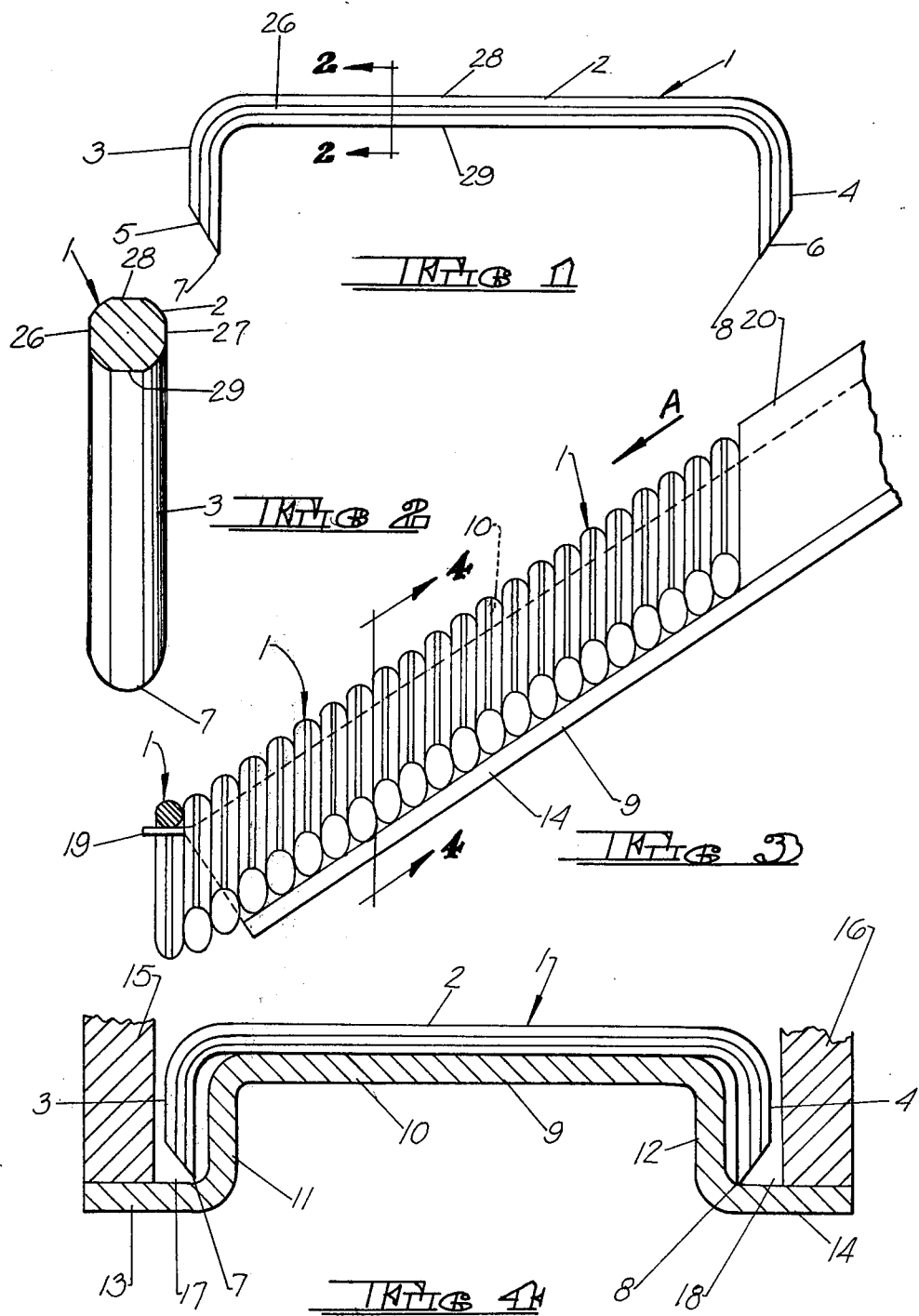

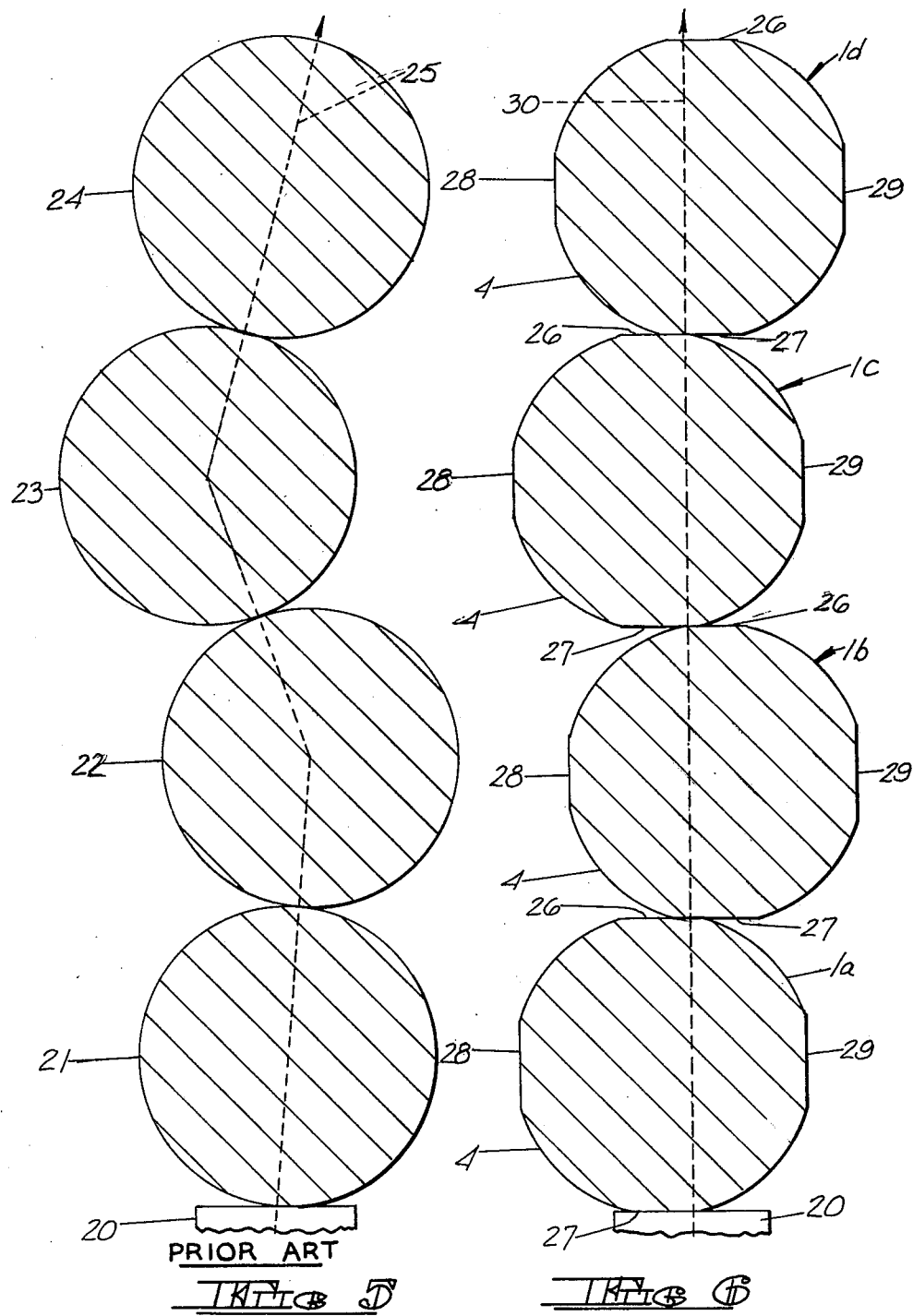

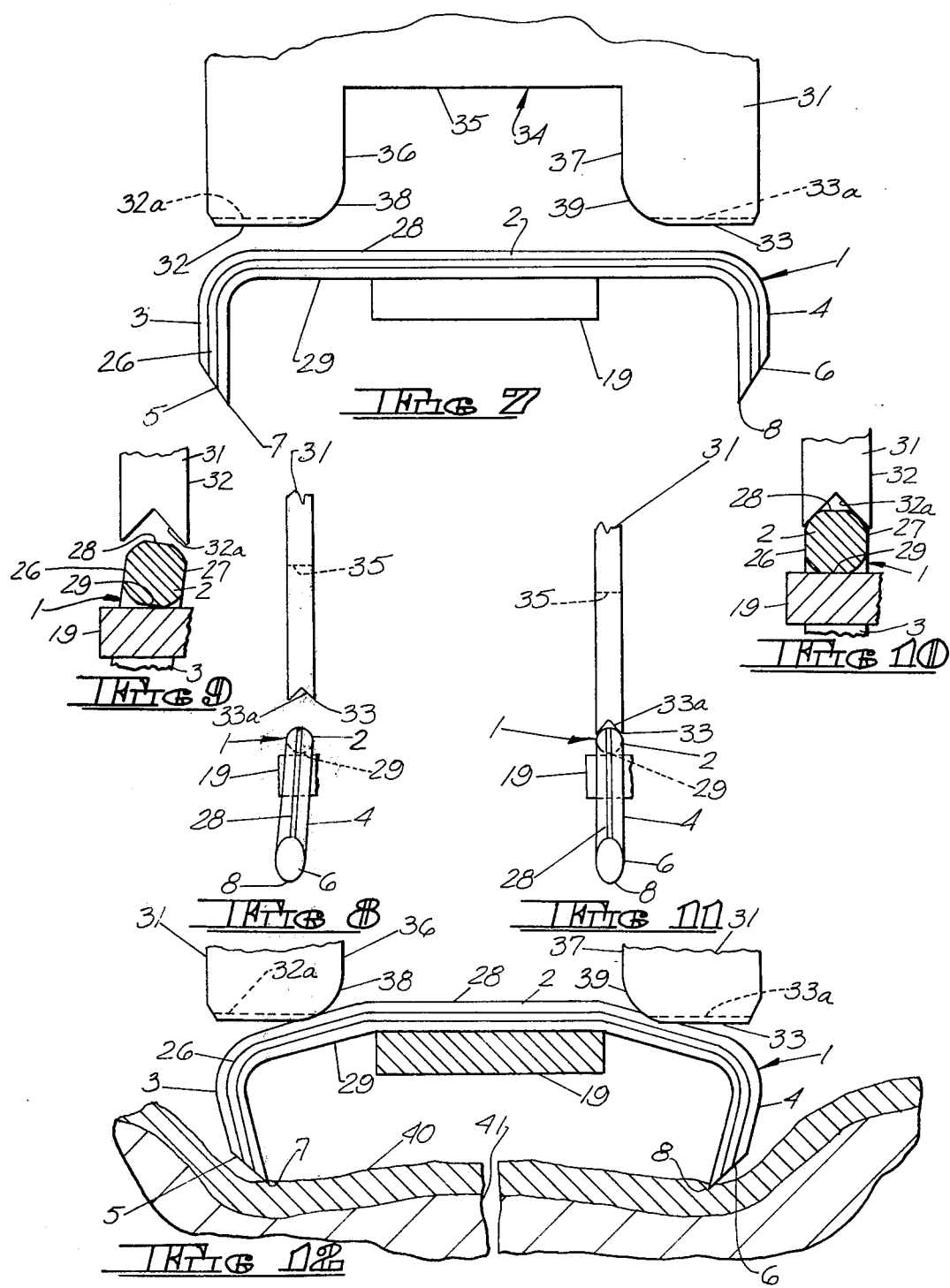

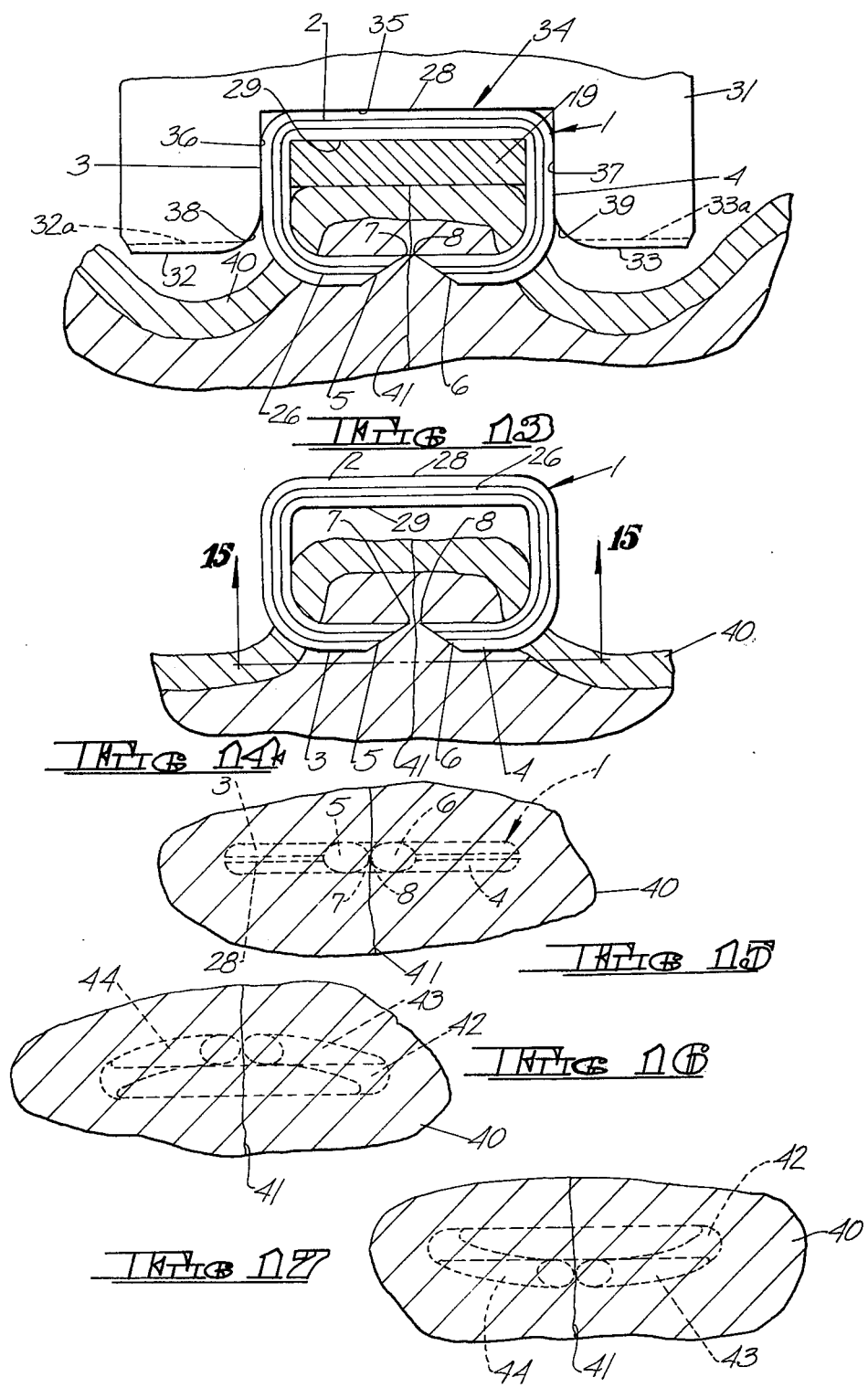

SURGICAL STAPLE

TECHNICAL FIELD

The invention relates to a surgical staple, and more particularly to a staple made of round wire having formed thereon four flats equally spaced about the wire circumference to assist in the feeding and forming of the surgical staple.

BACKGROUND ART

In recent years surgeons have come more and more to the use of surgical staples (sometimes referred to as staple sutures), rather than conventional thread sutures, for the closing of wounds or incisions in the skin or fascia of a patient. This is true in part because the use of surgical staples is a far easier procedure. Of even greater importance, however, is the fact that the use of surgical staples is very much faster. Thus, the time required for suturing can be substantially reduced, thereby reducing the length of time the patient must be maintained under anesthesia.

Prior art workers have developed various types of surgical stapling instruments. Many of these surgical stapling instruments are provided with staple carrying cartridges which include the staple forming anvil. In some embodiments, the staples are individually located on a flexible belt. This is taught for example in U.S. Pat. No. 3,650,453 and U.S. Pat. No. 3,837,555. U.S. Pat. No. 3,638,847 teaches a cartridge wherein the staples are located individually and one behind the other on a sawtooth staple-retaining member. In U.S. Pat. No. 3,618,842, the staples are located one above the other and are advanced by a pair of threaded screws. U.S. Pat. No. 4,043,504 teaches a cartridge having a staple feeding track wherein the staples are located one above the other and are advanced by a sinuous spring.

Prior art workers have also developed surgical stapling instruments wherein the staples are located in a tandem row in a more conventional staple feed housing. The forwardmost staple of the housing is caused to be shifted downwardly through a substantially vertical staple guide to an anvil by the staple former. Continued movement of the staple former results in the forming of the staple about the anvil. Such a surgical stapling instrument is taught in U.S. Pat. No. 3,873,016.

More recently, single use, disposable surgical stapling instruments have been devised wherein an anvil plate is provided having a central raised portion adapted to be straddled by a plurality of staples arranged in a tandem row. The downwardly depending legs of the staples are confined between the central raised portion of the anvil plate and adjacent vertical walls which may constitute either a part of the anvil plate or a part of the surgical stapling instrument, itself. The central raised portion of the anvil plate terminates at its forward end in an anvil having a coextensive anvil surface. Such surgical stapling instruments are taught in U.S. Pat. No. 4,109,844 and U.S. Pat. No. 4,179,057. In these surgical stapling instruments, the forwardmost staple of the row thereof, located on the anvil, is contacted by the staple former and is simultaneously formed about the anvil and implanted in the skin or fascia of the patient. While the surgical staple of the present invention is not so limited, it will be described in terms of its use with a disposable surgical stapling instrument of the type taught in the above noted U.S. Pat. No. 4,109,844 and the above noted copending application.

Surgical staples are relatively small and are normally made of metallic wire suitable for use in a surgical environment and of circular cross section. The wire is thin, generally having a diameter in the neighborhood of 0.020 inches.

Wire of circular cross section is used to form the surgical staples for a number of reasons. First of all, such wire is easier to make and is more readily available. It is free of sharp edges, easier to form and is more easily removable from the anvil and the former. The use of circular wire, however, has certain disadvantages. For example, as the staples are advanced along the surgical stapling instrument guide means, the fact that their cross section is circular tends to cause the staples to shift laterally with respect to the guide means. This tends to result in a jamming action between the guide means and the adjacent vertical walls of the surgical stapling instrument. To completely prevent this by spacing the adjacent walls from the guide means by a distance just sufficient to enable the staples legs to pass therethrough, would require the maintaining of tolerances which simply would not be practical, particularly in a disposable surgical instrument.

It has also been determined that the manufacture of surgical staples from wire having a circular cross section tends to promote rotation of the crown portion of the surgical staple prior to and during the forming and implanting thereof. As will be more fully described hereinafter, when this occurs it results in improper forming of the surgical staple.

The present invention is directed to the discovery that these problems can be overcome if the surgical staples are made of wire having four flats formed on its exterior surface at 0°, 90°, 180° and 270° about its circumference. The wire is formed into surgical staples in such a way that each surgical staple will have a flat extending along the upper surface of its crown portion and along the outsides of its downwardly depending leg portions. The surgical staple will have a diametrically opposed flat extending along the underside of its crown portion and down along the insides of its leg portions. This diametrically opposed pair of upper and lower flats will cooperate with the surgical stapling instrument anvil and staple former to prevent axial rotation of the crown during the forming and implanting of the surgical staple.

The surgical staple will also have a diametrically opposed pair of flats extending along the front and rear surfaces of its crown portion and its downwardly depending leg portions. As the tandem row of surgical staples is caused to travel along the guide means by an appropriate pusher element, adjacent surgical staples will contact each other flat-to-flat, eliminating that camming action caused by a circular cross section which tends to result in lateral shifting of the individual surgical staples on the guide means. In this way, the staple feed is greatly improved, by reducing the friction and tendency to jam caused by lateral shifting of the surgical staples.

It is known in the prior art to provide industrial staples and the like with an upper and lower diametrically opposed pair of flats. The purpose of these flats is to improve feeding of the staples on the arm of the staple manufacturing machine and during the application of glue to the staples to make up strips or "sticks" of staples. It will be understood by one skilled in the art that a glued stick of staples is not characterized by the feed problem described above. Surgical staples, on the other hand, are individual, not being formed into strips or sticks. For use in a surgical environment, each surgical staple must be sterile and free of glue or other foreign material.

DISCLOSURE OF THE INVENTION

According to the present invention there is provided in a surgical staple for use in suturing the skin or fascia of a patient and of the type having an elongated, substantially horizontal crown portion terminating in downwardly depending leg portions having points formed at their free ends, the surgical staple, together with a plurality of identical surgical staples, being adapted to straddle and to be fed along guide means and to the anvil of a surgical stapling instrument about which the crown is formed by a staple former of the surgical stapling instrument which bends end portions of the surgical staple crown downwardly so that the leg portions are substantially coaxial with their points approaching each other; the improvement comprising a first pair of diametrically opposed front and rear flats and a second pair of diametrically opposed top and bottom flats on the surgical staple. The front and rear flats of the first pair extend respectively along the front and rear of the crown and leg portions of the surgical staple. The diametrically opposed flats of the second pair are disposed at 90° to the first pair of flats. The top flat of the second pair extends along the upper surface of the surgical staple crown portion and the outsides of its leg portions and the bottom flat of the second pair extends along the underside of the surgical staple crown portion and along the insides of its leg portions. The front and rear flats of the first pair, cooperate with similar flats on adjacent surgical staples, to assure proper feeding of the surgical staple along the surgical instrument guide means. The top and bottom flats of the second pair, cooperate respectively with the surgical stapling instrument former and anvil, to prevent undesirable axial rotation of the surgical staple crown portion during the forming and implanting thereof in the skin or fascia of a patient.

BRIEF DESCRIPTION OF THE DRAWINGS

FIG. 1 is a front elevational view of a surgical staple of the present invention.

FIG. 2 is a cross sectional view taken along section line 2—2 of FIG. 1.

FIG. 3 is a fragmentary side elevational view, partly in cross section, illustrating a plurality of surgical staples of the present invention arranged in a tandem row on the anvil and guide means of a surgical stapling instrument.

FIG. 4 is a cross sectional view taken along section line 4—4 of FIG. 3.

FIG. 5 is a semi-diagrammatic, cross sectional view through one set of legs of a plurality of prior art surgical staples.

FIG. 6 is a semi-diagrammatic, cross sectional view, similar to FIG. 5 and illustrating one set of legs of a plurality of surgical staples of the present invention.

FIG. 7 is a fragmentary front elevational view illustrating a surgical staple of the present invention and an exemplary anvil and former of a surgical stapling instrument.

FIG. 8 is a fragmentary side elevational view of the staple and the surgical stapling instrument anvil and former of FIG. 7, and showing the surgical staple with its crown portion rotated slightly about its axis so as to shift the staple leg portions forwardly.

FIG. 9 is a fragmentary enlarged view, partly in cross section, illustrating the staple crown portion and the anvil of FIG. 8.

FIG. 10 is a fragmentary cross sectional view similar to FIG. 9 but illustrating the surgical stapling instrument former in contact with the surgical staple crown portion resulting in a "squaring" of the staple with respect thereto and to the surgical stapling instrument anvil.

FIG. 11 is a fragmentary side elevational view similar to FIG. 8 and illustrating the "squared" staple of FIG. 10.

FIG. 12 is a fragmentary elevational view, partly in cross section, illustrating the initial stage of the formation of the surgical staple with its points entering the skin to either side of an incision to be closed.

FIG. 13 is a fragmentary elevational view, partly in cross section, similar to FIG. 12 and illustrating the surgical staple at the end of the forming operation.

FIG. 14 is a fragmentary elevational view, partly in cross section, illustrating the fully formed and implanted staple closing the incision.

FIG. 15 is a framentary cross sectional view taken along section line 15—15 of FIG. 14.

FIGS. 16 and 17 are fragmentary cross sectional views similar to FIG. 15 and illustrating the surgical staple when improperly formed.

DETAILED DESCRIPTION OF THE INVENTION

The surgical staple of the present invention is illustrated in FIGS. 1 and 2. The surgical staple is generally indicated at 1 and comprises a wire-like structure of invert U-shaped configuration having a substantially horizontal, elongated crown portion 2 terminating at its ends in downwardly depending leg portions 3 and 4. The free ends of leg portions 3 and 4 are cut at a slant (as at 5 and 6, respectively) to cause the free ends of the legs to terminate in points 7 and 8, respectively.

Referring now to FIGS. 3 and 4, a plurality of the surgical staples 1 are illustrated as being arranged in a tandem row on a surgical stapling instrument guide means 9. For purposes of an exemplary showing, the guide means 9 is illustrated as being an anvil plate of the type taught in the above mentioned copending application. As is most clearly shown in FIG. 4, the elongated anvil plate has an inverted U-shaped cross section. The anvil plate 9 comprises a raised central portion 10 terminating at its edges in downturned portions 11 and 12. The portions 11 and 12, in turn, terminate in lateral flange portions 13 and 14, respectively. Side portions 15 and 16 of the surgical stapling instrument (FIG. 4) cooperate with the flange portions 13 and 14 and the downwardly depending portions 11 and 12 of the anvil plate 9 to form elongated channels 17 and 18. The channels 17 and 18 are in parallel spaced relationship, being separated by the central portion 10 of the anvil plate. As is clearly shown in FIGS. 3 and 4, the staples 1, arranged in a tandem row, straddle the central portion 10 of anvil plate 9 with the crown portion 2 of each staple contacting the upper surface of anvil plate portion 10. The staple leg portions 3 and 4 travel in channels 17 and 18, respectively, with the points 7 and 8 of each staple contacting anvil plate lateral flanges 13 and 14, respectively.

As is shown in FIG. 3, the forwardmost end of anvil plate 9 terminates in an anvil 19. As will be shown hereinafter, each surgical staple during the implanting procedure is formed about this anvil 19. As is clearly shown in FIG. 3, the upper surface of the central portion 10 of anvil plate 9 is coextensive with the upper surface of anvil 19. While these surfaces may also be coplanar, in the particular embodiments taught in the above mentioned U.S. Pat. No. 4,109,844 and the above mentioned copending application, the anvil plate portion 10 lies at an angle of about 30° to the anvil 19.

In FIG. 3, the forwardmost surgical staple 1 of the row thereof is shown in cross section, positioned upon anvil 19. This forwardmost staple is therefore in position to be formed and implanted. When the first surgical staple of the row is formed, implanted and removed from anvil 19, the row of staples will be shifted forwardly to locate the next succeeding surgical staple on anvil 19. This is accomplished by a staple advancing shoe 20, fragmentarily shown in FIG. 3. The shoe 20 straddles the central portion of the anvil plate in much the same way as do the surgical staples and contacts at least the leg portions of the last staple of the row (the shoe may also contact the crown portion of this last staple, depending upon its design). The shoe applies a nearly constant forward force to the last staple (and therefore to the entire row) in the direction of arrow A. To accomplish this, the shoe 20 may be constantly urged forwardly by any appropriate means (not shown) such as a spring, a spring biased pawl, or the like.

Returning to FIG. 4, the width of channels 17 and 18 has been exaggerated for purposes of clarity. Nevertheless, it is apparent from FIG. 4 that the staple 1 could shift laterally (i.e., transversely) with respect to the central raised portion 10 of anvil plate 9 and toward the surgical staple instrument side portions 15 or 16. To so size channels 17 and 18 as to permit the legs to pass therethrough while precluding such lateral shifting of the surgical staples is simply not practical, particularly in a single-use, disposable surgical stapling instrument. This results in a problem which is semi-diagrammatically illustrated in FIG. 5. FIG. 5 is a cross-sectional view through the leg portions 21 through 24 of a series of prior art surgical staples made of wire of circular cross section. The prior art staples may be considered to be mounted on an anvil plate of the type shown in FIGS. 3 and 4. A fragmentary portion of the staple advancing shoe 20 is shown applying a forward force to staple leg 21 and therefore to all of staple legs 21 through 24. The force is indicated by broken-line arrow 25.

By virtue of the circular cross section of legs 21 through 24, the force (indicated by arrow 25) tends to pass through the centers of these legs, and their points of tangency. Their circular cross section tends to cause the legs to cam each other, either to the left or to the right. Thus, legs 21 and 23 tend to urge leg 22 to the right, while legs 22 and 24 tend to urge leg 23 to the left, all as viewed in FIG. 5. This lateral shifting of the legs may cause them to come in contact with the downwardly depending portions 11 and 12 of the anvil plate or the adjacent side portions 15 and 16 of the surgical stapling instrument (see FIG. 4). If the staple legs are forced against these elements, a increased frictional engagement results which impedes proper forward feeding of the row of staples and, if sufficiently severe, can result in jamming.

Returning to FIGS. 1 and 2, it will be noted that the surgical staple 1 is made up of wire of circular cross section having two pairs of diametrically opposed flats formed thereon. The first pair is made up of flats 26 and 27, while the second pair is made up of slats 28 and 29. The first pair of diametrically opposed flats 26 and 27 are oriented at 90° to the second pair of diametrically opposed flats 28 and 29 so that, for purposes of description, if flat 26 is considered as lying at 0° about the circumference of the staple, then flat 28 is located at 90° while flats 27 and 29 are located at 180° and 270°, respectively.

Flat 26 is located on what may be termed, for purposes of this description, the front surface or face of the staple 1. By this is meant, that surface of the staple which faces forwardly toward anvil 19 (FIG. 3). It will be noted that the flat 26 (hereafter termed the front flat) extends along the crown portion 2 and the downwardly depending leg portions 3 and 4 of the staple. In a similar fashion, diametrically opposed flat 27 is located on what may be termed the rear face or surface of the surgical staple 1, i.e., that surface which faces rearwardly away from anvil 19. It will be evident from FIG. 2 that flat 27 (hereafter termed the rear flat) also extends along the full length of the surgical staple crown portion 2 and the downwardly depending leg portions 3 and 4.

FIG. 6 is a semi-diagrammatic cross-sectional view (similar to FIG. 5) through the legs 4 of a plurality of surgical staples of the type shown at FIGS. 1 and 2 when arranged in a tandem row on anvil plate 9 as shown in FIGS. 3 and 4. Once again, a fragmentary portion of the staple advancing shoe 20 is shown. For purposes of explanation, the staples in FIG. 6 have been designated 1a through 1d. The cross sectional view is taken through the leg portion 4 of each of these surgical staples and the flats 26 through 29 are shown for each staple.

When arranged in a tandem row as shown in FIG. 6, it will be noted that the front flat 26 on the forward face of each staple leg 4 is in abutment with rear flat 27 on the rear face of the adjacent staple leg. This is true for all but the forwardmost and rearwardmost surgical staples of the tandem row. The forwardmost staple 1d of course has no additional staple ahead of it for its front flat 26 to contact. The rearwardmost staple 1a has its rear flat 27 engaged by the staple advancing shoe 20. Since the tandemly arranged surgical staples 1a through 1d contact each other along their leg portions flat-to-flat, the force exerted by surgical staple advancing shoe 20, which is indicated by broken line arrow 30, constitutes a straight line passing through the abutting flats 26 and 27. It will be evident from FIG. 6 that there are no components of force tending to urge the staple legs 4 laterally.

It will be understood that the leg portions 3 of the surgical staples 1a through 1d will similarly be arranged flat-to-flat and a broken arrow similar to arrow 30 could be drawn through them in the same fashion. As a result, surgical staple leg portions 3 will not be urged strongly against either the vertical portion 11 of the anvil plate 9 or the side portion 15 of the surgical stapling instrument (see FIG. 4) and the same is true of surgical staple leg portions 4 with respect to vertical anvil plate portion 12 and surgical instrument side portion 16. As a result, the feeding of the surgical staples along anvil plate 9 is accomplished with reduced friction and any tendency to jam by virtue of lateral shifting of the staples is virtually eliminated.

It will further be understood by one skilled in the art that if the anvil plate 9 were horizontal, as is true of the staple guide means of the surgical stapling instrument of the above mentioned U.S. Pat. No. 3,873,016, those portions of front and rear flats 26 and 27 extending along the surgical staple crown portions would also cooperate in precisely the same manner to eliminate any tendency of the surgical staples to be urged downwardly against the guide means or to be lifted away therefrom. This would further enhance the feeding of the staples in a surgical stapling instrument having a horizontal staple guide means.

FIG. 7 illustrates the surgical staple 1 of FIGS. 1 and 2 located on the upper surface of anvil 19 in position to be formed thereabout. Above surgical staple 1 there is fragmentarily shown the bottom end of a staple former 31 of a surgical stapling instrument. As will be evident hereinafter, the staple former 31 is shiftable by the surgical stapling instrument from an upper or retracted position to a lower or advanced position in which it forms the staple about anvil 19. The staple former 31 has a pair of horizontal lower edges 32 and 33 separated from each other by a notch generally indicated at 34. The notch 34 is defined by an upper horizontal edge 35 and a pair of downwardly extending vertical side edges 36 and 37. The vertical side edge 36 of notch 34 is connected to the bottom horizontal edge 32 by a curved edge portion 38. Similarly, the vertical edge 37 of notch 34 is connected to the bottom horizontal edge 33 by a curved edge portion 39.

As an option, the lower horizontal edges 32 and 33 of staple former 31 may have V-shaped notches formed therein, as at 32a and 33a. The notch 33a is clearly shown in FIGS. 8 and 9 and it will be understood that the V-shaped notch 32 is substantially identical. It will be evident from FIG. 7 that as the staple former is shifted downwardly, its lower horizontal edge portions 32 and 33 will make first contact with the surgical staple 1 against the crown portion 2 thereof. The V-shaped notches 32a and 33a may be provided to assure proper transverse alignment of the surgical staple 1 on an anvil 9.

It has been found that prior to and especially during the staple forming operation, there is a tendency for the crown portion 2 of the surgical staple 1 to rotate about its axis on the anvil 19. This axial rotation of the staple crown portion 2 results in a shifting of the staple leg portions 3 and 4 either forwardly or rearwardly, a condition often referred to as "leg roll". As will be shown hereinafter, such rotation of the staple crown portion 2 and such forward or rearward shifting of staple leg portions 3 and 4 result in an undesirable malformation of the legs, rendering the surgical staple more painful to the patient during extraction, and, if sufficiently malformed, impairing the suturing ability of the surgical staple. FIG. 8 is an end elevational view of the structure of FIG. 7. FIG. 9 is an enlarged, fragmentary cross section view thereof. The staple former 31 is again illustrated in its elevated or retracted position. FIGS. 8 and 9 differ from FIG. 7 in that the surgical staple 1 is shown mounted on the anvil 19 with its crown portion 2 having undergone sufficient axial rotation as to produce a forward leg roll.

FIGS. 10 and 11 are similar to FIGS. 9 and 8 respectively and illustrate initial contact between the staple former 31 and the surgical staple 1. As the staple former 31 initially contacts the surgical staple 1, the V-shaped notches 32 and 33 will first assure proper transverse alignment of the surgical staple 1 on the anvil 19. As pressure is applied to the crown portion 2 of the surgical staple 1 by the staple former 31, the flat 29 (located on the underside of staple crown portion 2 and on the insides of staple leg portions 3 and 4 and hereafter termed the bottom flat) will cooperate with the upper surface of anvil 19 to cause the staple to "square" or "right" itself on the anvil 19 assuring that the staple leg portions 3 and 4 are properly perpendicularly oriented with respect to the upper surface of the anvil 19, as shown in FIG. 11. If the bottom horizontal edges 32 and 33 of staple former 31 are not notched, these bottom edges, themselves will cooperate with the staple flat 28 (running along the upper part of surgical staple crown portion 2 and along the outsides of surgical staple leg portions 3 and 4 and hereafter called the top flat) to further assist in "righting" the surgical staple 1 with respect to the anvil 19.

FIG. 12 is similar to FIG. 7 but ilustrates the former 31 at its position immediately after initial contact and at the time when the actual forming of the surgical staple 1 begins and its points 7 and 8 begin to enter the skin 40 of a patient to close or suture the wound 41 therein. It will be evident from FIG. 12 that the end portions of the surgical staple crown portion 2 are beginning to be bent about the anvil 19. At the same time, these bent end portions of the surgical staple crown 2 are exiting the V-shaped notches 32a and 33a of staple former 31 and are beginning to be contacted by the curved edge portions 38 and 39 thereof. These un-notched curved edge portions 38 and 39 cooperate with the top flat 28 of the surgical staple 1 (the bottom flat 29 still cooperating with the upper surface of anvil 19) to assure against rotation of the surgical staple crown portion 2 and consequent leg roll during staple formation.

FIG. 13 is a view similar to FIG. 12 (like parts having been given like index numerals), but illustrating the staple former 31 at the bottom of its stroke and the surgical staple 1 in its fully formed condition. It will be evident from FIG. 13 that as the staple former 31 continues its downward travel, the top flat 28 of surgical staple 1 will be contacted by the curved edge portions 38 and 39 of staple former 31 and thereafter by the vertical staple former edges 36 and 37. Finally, it will not only remain in contact with staple former edges 36 and 37, but ultimately will be contacted by staple former edge 35. At the same time, the bottom flat 29 of surgical staple 1 remains in part at least in contact with the upper surface of anvil 19 and in contact with the side edges of the anvil 19. During the forming, the central part of surgical staple crown portion 2 may tend to lift slightly from the upper surface of anvil 19 until compressed by the staple former edge 35. Nevertheless, the bottom flat 29 will remain in contact with the anvil edges. This constant contact of the top flat 28 by various edges of staple former 31 and constant contact of the bottom flat 29 with the upper and/or edge surfaces of anvil 19 will assure against crown rotation and leg roll throughout the staple forming and implanting procedure.

FIGS. 14 and 15 illustrate the fully formed and implanted staple after removal of the surgical stapling instrument. Again, like parts have been given like index numerals. As is evident from FIGS. 13 and 14, the fully formed staple takes on a sort of box-like shape. When properly formed and implanted, its points 7 and 8 approach each other and its leg portions 3 and 4 are substantially coaxial (See FIGS. 14 and 15). FIG. 16 is similar to FIG. 15, but illustrates a surgical staple 42, not provided with flats, and having been formed while exhibiting forward leg roll. It will be apparent that the leg portions 43 and 44 do not have their ends pointing directly toward each other and are not substantially coaxial. FIG. 17 is similar to FIG. 16 and again illustrates a typical surgical staple of circular cross section without the flats of the present invention. Like parts have again been given like index numerals. FIG. 17 differs from FIG. 16 in that it illustrates an implanted staple which has undergone rearward leg roll during the forming and implanting procedure. Again it will be noted that the points of the staple are not directly approaching each other and that the staple leg portions 43 and 44 are not substantially coaxial. It will be evident from FIGS. 16 and 17 that a staple implanted in skewed condition as shown in these figures, when removed with an appropriate extractor, such as that taught in U.S. Pat. No. 4,026,520, may cause more pain to the patient.

While the flats 26 through 29 could be formed on surgical staple 1 by coining or the like, it is easier and preferred to make the surgical staple 1 from wire having these flats already thereon. The width of flats 26 through 29 may range from the narrowest dimension which will still enable the flats to achieve the above stated purposes to a width such that the surgical staple is nearly square or rectangular in cross section. The use of a wire of square or rectangular cross section, as opposed to a wire of circular cross section having the four flats 26 through 29 formed thereon, is undesirable for several reasons. A staple of square or rectangular cross section has sharp edges and is more difficult to form. During the forming process, at the points where the staple is bent, bulges will occur in the wire (usually in about the lower one-third of the wire due to material compression). These bulges may interfere with the proper placement of the staples in a tandem row and may add to the tendency of the row of staples to jam. Furthermore, staples made of square or rectangular wire are more difficult to remove both from the surgical instrument anvil and the staple former.

The lower end of the range of the width of the flats 26 through 29 is governed not only by the requirement of a flat width sufficient to enable the flats to serve their intended purpose, but also by a matter of practicality with respect to the ease of forming such flats on a wire of circular cross section. It is well within the skill of the worker in the art, armed with the teachings of this application, to determine an ideal width for flats 26 through 29 to suit his purposes, taking into account the above noted factors, together with the diameter of the wire from which the staples are formed and the size of the staples. As a non-limiting example, excellent results have been achieved through the use of a surgical stapling instrument of the type taught in the above noted copending application and staples made of wire of 0.020 inch diameter having flats of a width of 0.005 inch formed thereon. As a general rule of thumb, the width of the flats 26 through 29 should be from at least about one tenth the diameter of the circular wire from which the staple is made up to a maximum width wherein there still remains an arcuate surface between adjacent ones of the flats. It will be understood that the top and bottom flats 28 and 29 need not be of the same width as the front and rear flats 26 and 27.

Modifications may be made in the invention without departing from the spirit of it. For example, the surgical staple of the present invention may be provided with just one of said pairs of diametrically opposed flats.

What is claimed is:

1. A surgical staple for use with a surgical stapling instrument of the type having a guide means to be straddled by a plurality of said surgical staples arranged in a tandem row, an anvil, means to advance said staple along said guide means toward said anvil and a staple former to form said staple about said anvil and simultaneously implant said staple in the skin or fascia of a patient to close an incision therein, said surgical staple comprising a piece of wire having an elongated horizontal crown portion terminating at its ends in downwardly depending leg portions, said leg portions each having a point formed at its free end, and a pair of diametrically opposed flats on said surgical staple, the portions of said staple between said flats forming convex cylindrical surfaces, said flats of said pair extending respectively along the front and rear of said staple crown portion and said leg portions, said flats being so located on said surgical staple that when said surgical staple is arranged in a tandem row of identical surgical staples, said flats will lie in abutting relationship with similar flats on adjacent ones of said surgical staples whereby to improve the advancing of said surgical staples along said surgical stapling instrument guide means.

2. The structure claimed in claim 1 including a second pair of diametrically opposed flats formed on said surgical staple, said second pair of flats being oriented at 90° to said first mentioned pair of flats, one of said flats of said second pair extending along the top of said crown portion and along the outsides of said leg portions, the other of said flats of said second pair extending along the bottom of said crown portion and the insides of said leg portions, said first mentioned flat of said second pair cooperating with said staple former and said second flat of said second pair cooperating with said anvil to prevent rotation of said crown portion on said anvil during formation of said staple.

3. The structure claimed in claim 2 wherein each of said flats has a width of at least one-tenth the diameter of said wire.

* * * * *